United States Patent
Ku et al.

(10) Patent No.: US 9,945,874 B2
(45) Date of Patent: *Apr. 17, 2018

(54) MARKER FOR DIAGNOSING DIABETIC RETINOPATHY AND USE THEREOF

(71) Applicants: LG Electronics Inc., Seoul (KR); SNU R&DB FOUNDATION, Seoul (KR)

(72) Inventors: Yunhee Ku, Seoul (KR); Yongju Yang, Seoul (KR); Youngsoo Kim, Seoul (KR); Jonghwa Jin, Seoul (KR); Kyunggon Kim, Gyeonggi-do (KR); Moosub Kim, Seoul (KR); Seungyeon Song, Seoul (KR)

(73) Assignees: LG ELECTRONICS INC., Seoul (KR); SNU R&DB FOUNDATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/869,270

(22) Filed: Sep. 29, 2015

(65) Prior Publication Data

US 2016/0018415 A1    Jan. 21, 2016

Related U.S. Application Data

(62) Division of application No. 13/921,026, filed on Jun. 18, 2013.

(30) Foreign Application Priority Data

Jun. 27, 2012 (KR) ........................ 10-2012-0069027

(51) Int. Cl.
 *C12Q 1/68* (2018.01)
 *G01N 33/68* (2006.01)

(52) U.S. Cl.
 CPC ....... *G01N 33/6893* (2013.01); *C12Q 1/6881* (2013.01); *C12Q 1/6883* (2013.01); *C12Q 2600/158* (2013.01); *G01N 2333/4716* (2013.01); *G01N 2333/8114* (2013.01); *G01N 2800/164* (2013.01)

(58) Field of Classification Search
 None
 See application file for complete search history.

(56) References Cited

U.S. PATENT DOCUMENTS

| | | |
|---|---|---|
| 2009/0186032 A1 | 7/2009 | Kim et al. |
| 2009/0214538 A1 | 8/2009 | Fung et al. |
| 2010/0166862 A1 | 7/2010 | Francois et al. |
| 2010/0179307 A1 | 7/2010 | Kim et al. |
| 2012/0135430 A1 | 5/2012 | Zhang et al. |

OTHER PUBLICATIONS

Yasojima et al. Up-regulated production and activation of the complement system in Alzheimer's disease brain. Amer. J. Pathology (1999) vol. 154, No. 3, pp. 927-936.*
Reichwald et al. Expression of complement system components during aging and amyloid deposition in APP transgenic mice. J. Neuroinflammation (2009) 6:35, pp. 1-12, including Additional file 1.*
Geisert et al. Expression of inter-alpha-trypsin inhibitor heavy chains in endometrium of cyclic and pregnant gilts. Reproduction (2003) vol. 126, pp. 621-627.*
Bossi et al. C7 is expressed on endothelial cells as a trap for the assembling terminal complement complex and may exert anti-inflammatory function. Blood (2009) vol. 113, No. 15, pp. 3640-3648.*
Kim et al., "Verification of Biomarkers for Diabetic Retinopathy by Multiple Reaction Monitoring," Journal of Proteome Research (2010), vol. 9, pp. 689-699.

* cited by examiner

*Primary Examiner* — David C Thomas
(74) *Attorney, Agent, or Firm* — Birch, Stewart, Kolasch & Birch, LLP

(57) ABSTRACT

The present invention relates to a marker which can be used to diagnose a diabetic retinopathy patient and determine the progression of diabetic retinopathy, a composition for diagnosing diabetic retinopathy, which comprises an agent for measuring the level of a gene or protein associated with the marker, and the use thereof.

4 Claims, 7 Drawing Sheets
(1 of 7 Drawing Sheet(s) Filed in Color)

(left) non-proliferative diabetic retinopathy (NPDR)

(right) proliferative diabetic retinopathy (PDR)

MARKER FOR DIAGNOSING DIABETIC RETINOPATHY AND USE THEREOF

CROSS-REFERENCE TO RELATED APPLICATIONS

The present application is a 37 C.F.R § 1.53(b) divisional of U.S. application Ser. No. 13/921,026 filed Jun. 18, 2013, which claims priority on Korean Patent Application No. 10-2012-0069027 filed Jun. 27, 2012. The entire contents of each of these applications is hereby incorporated by reference.

BACKGROUND OF THE INVENTION

Field of the Invention

The present invention relates to a marker for diagnosing diabetic retinopathy, a composition for diagnosing diabetic retinopathy, and a kit for diagnosing diabetic retinopathy. Moreover, the present invention relates to an analysis method for providing information required for the diagnosis of diabetic retinopathy.

Description of the Prior Art

Generally, diabetes is accompanied by various complications and typically causes cardiovascular diseases, diabetic nephropathy, diabetic neuropathy, diabetic retinopathy, etc.

Among them, diabetic retinopathy (DR) is diagnosed in 60% or more of diabetics within 10 years after diagnosis and 90% or more of diabetics within 20 years after diagnosis. Diabetic retinopathy is a microangiopathy caused by diabetes, and the features thereof include alterations in retinal vasculature, vascular occlusion, ischemia, neovascularization, and fibrovascular proliferation. Diabetic retinopathy is the most common cause of loss of vision in adults, and in USA, 12,000-24,000 diabetics lose their vision each year. According to a study, the prevalence of diabetic retinopathy is estimated to be about 40% of diabetics in the USA, and about 8% thereof can lead to loss of vision. Diabetic retinopathy can be classified into early stage, non-proliferative diabetic retinopathy (NPDR) and late-stage, proliferative diabetic retinopathy (PDR) (FIG. 1).

In non-proliferative diabetic retinopathy (NPDR), retinal bleeding, microaneurysm, exudate, retinal edema and the like appear due to the occlusion and change in permeability of retinal capillaries while vision is weakened little by little. In addition, it may be accompanied by diabetic macular edema (DME), and in this stage, vision can be severely reduced.

Proliferative diabetic retinopathy (PDR) is a stage in which ischemia is caused by the occlusion of retinal vessels, and thus neovascularization proliferates. This proliferation progresses from the retina to the vitreous body, and complications, including vitreous hemorrhage caused by vitreoretinal traction, tractional retinal detachment, neovascular glaucoma, etc., occur, and loss of vision progresses.

For diabetic retinopathy, laser treatment or vitreous surgery is generally performed, but there are still many patients in which diabetic retinopathy continues to progress, leading to loss of vision. For this reason, there is an increased need for the early diagnosis and inhibition of progression of diabetic retinopathy and the early treatment of a high-risk group. However, the cause of diabetic retinopathy has not yet been clearly established, and biomarkers for determining the progression of diabetic retinopathy are very limited.

Until now, studies on diabetic retinopathy have been conducted with a focus on biochemical and molecular biological studies on the individual proteins of the vitreous body. In addition, studies on proteins in diabetic retinopathy are also in the stage of profiling (discovery) of vitreous proteins, in which proteins in the vitreous body of patients are identified by 2-DE and mass spectrometry. There are little or studies on the verification and validation of whether these vitreous proteins are expressed in blood or whether these can be used as clinical biomarkers.

Accordingly, there is a need to develop a novel diagnostic marker having high clinical specificity and sensitivity together with an antibody capable of detecting the marker in order to make it possible to early diagnose diabetic retinopathy and easily predict the progression thereof. In addition, there is a need to discover a biomarker for diagnosing non-proliferative diabetic retinopathy (NPDR) in which there is almost no subjective symptom.

Under such circumstances, the present inventors have made extensive efforts to develop a marker useful for the early diagnosis of diabetic retinopathy, and as a result, have discovered a protein specific to diabetic retinopathy and identified a protein, the expression of which increases or decreases in patients having diabetic retinopathy, by a LC-MS/MS method, thereby completing the present invention.

SUMMARY OF THE INVENTION

It is an object of the present invention to provide a marker for diagnosing diabetic retinopathy, which is selected from among the novel markers C7, ITIH2 and C5 capable of early diagnosing diabetic retinopathy and effectively diagnosing the progression thereof.

Another object of the present invention is to provide a composition for diagnosing diabetic retinopathy, which comprises an agent for measuring the level of mRNA or protein of at least one gene selected from among the above markers.

Still another object of the present invention is to provide a kit for diagnosing diabetic retinopathy, which comprises the above composition.

Still another object of the present invention is to provide a method for providing information required for diagnosis of diabetic retinopathy using the above composition or kit.

To achieve the above objects, in one aspect, the present invention provides at least one marker for diagnosing diabetic retinopathy, which is selected from among C7 (complement component C7), ITIH2 (inter-alpha-trypsin inhibitor heavy chain H2) and C5 (complement C5).

As used herein, the term "diabetic retinopathy" refers to a complication in which peripheral arterial disease is caused by diabetes so that the retinal microcirculation is altered to reduce vision.

As used herein, the term "diagnosis" means identifying the presence or nature of a pathologic condition. For the purpose of the present invention, the term "diagnosis" means identifying the onset of diabetic retinopathy. Specifically, it means the early stage, non-proliferative diabetic retinopathy.

As used herein, the term "marker for diagnosing" is meant to include organic biomolecules, polypeptides, nucleic acids (e.g. mRNA), lipids, glycolipids, glycoproteins, sugars (monosaccharide, disaccharide, oligosaccharide, etc.) and the like, the expression levels of which significantly increases or decreases in a subject having non-proliferative diabetic retinopathy compared to a normal control group (subject having no diabetic retinopathy) or a subject having proliferative diabetic retinopathy.

The present inventors have found that the above-described markers are effective in diagnosing diabetic retinopathy in the plasma of NoDR (nondiabetic retinopathy) patients (diabetics other than NPDR patients) and NPDR patients. PDR patients can be easily diagnosed by an ophthalmic method, because the symptoms of PDR are very extreme, and the subjective symptoms of the patients, including a rapid loss of vision, rapidly progress, and thus it is not effective to diagnose PDR using a separate molecule. However, NPDR patients are difficult to early diagnose by an ophthalmic method, because the development of symptoms of NPDR is insignificant, and the subjective symptoms of the patients are also very slow. Thus, the present invention provides a method for determining the expression levels of markers in NoDR and NPDR.

BRIEF DESCRIPTION OF THE DRAWINGS

The patent or application file contains at least one or more color drawings. Copies of this patent or patent application publication with color drawings will be provided by the USPTO upon request and payment of the necessary fee.

DETAILED DESCRIPTION OF THE INVENTION

Figure 1:
FIG. 1 is a set of photographs showing the eyeballs of a non-proliferative diabetic retinopathy patient and a proliferative diabetic retinopathy patient.
Figure 1:
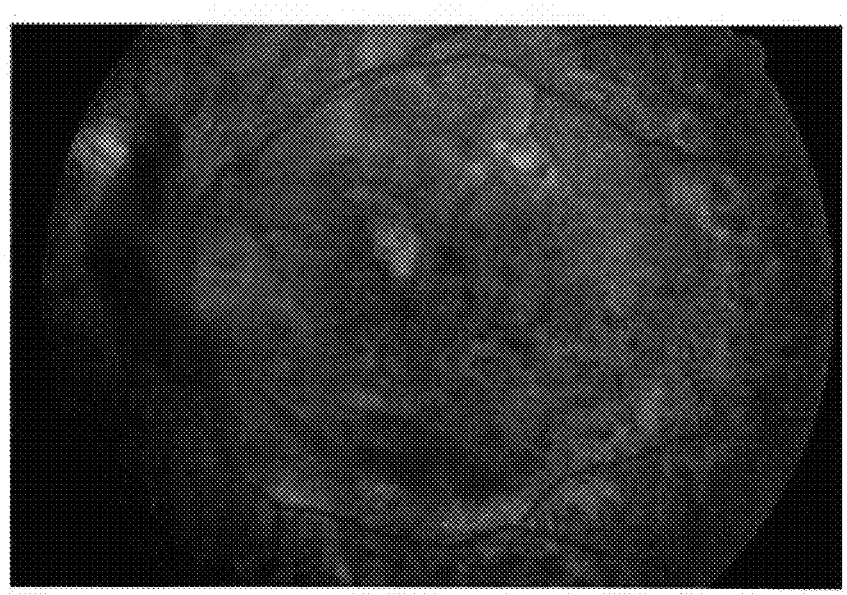
Figure 2:
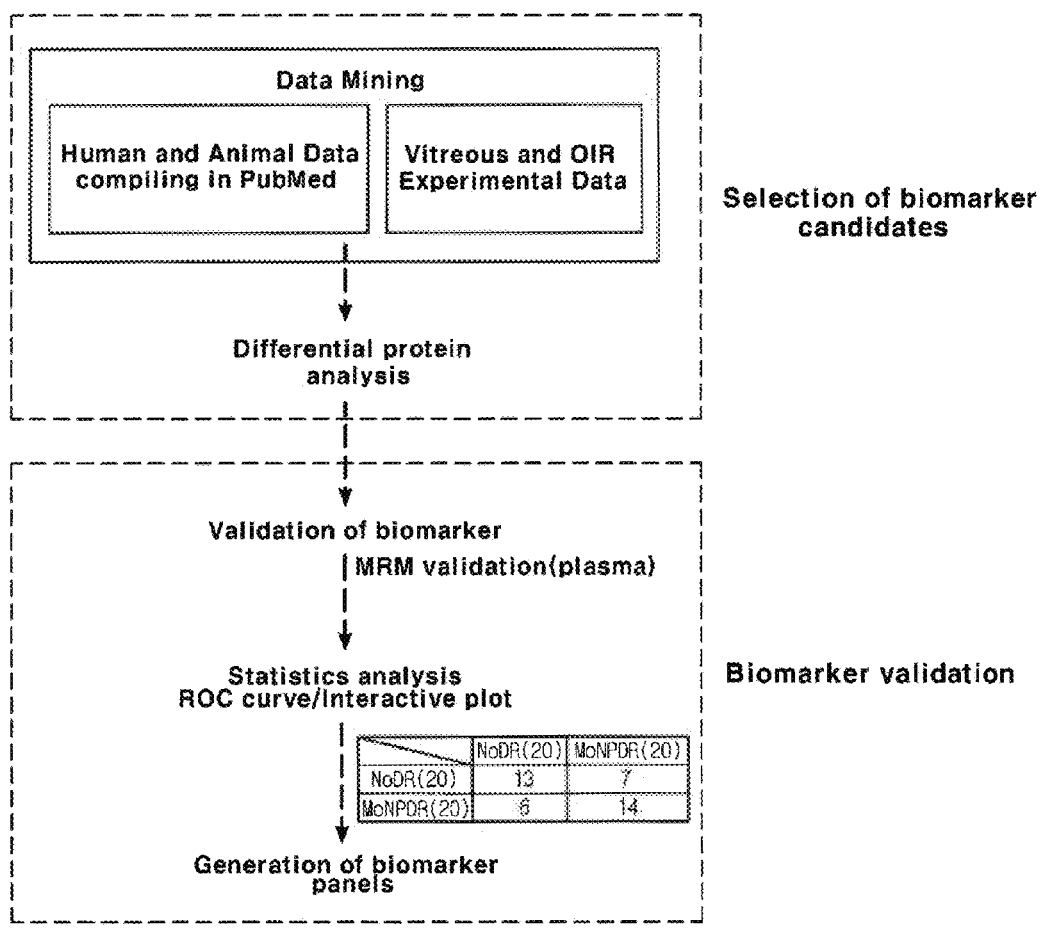
FIG. 2 is a flow chart showing the processes of Examples 1 to 6 of the present invention.

Although the present invention can be modified variously and have several embodiments, exemplary embodiments are illustrated in the accompanying drawings and will be described in detail in the detailed description. However, the present invention is not limited to the specific embodiments and should be construed as including all the changes, equivalents and substitutions included in the spirit and scope of the present invention. In the following description, the detailed description of related known technology will be omitted when it may obscure the subject matter of the present invention.

Terms used in this specification are used only to describe a specific embodiment and are not intended to limit the scope of the present invention. Singular expressions include plural expressions unless specified otherwise in the context thereof. In this specification, the terms "comprise", "have", etc., are intended to denote the existence of mentioned characteristics, numbers, steps, operations, components, parts, or combinations thereof, but do not exclude the probability of existence or addition of one or more other characteristics, numbers, steps, operations, components, parts, or combinations thereof.

A marker for diagnosing diabetic retinopathy according to the present invention may be at least one selected from among C7 (complement component C7), ITIH2 (inter-alpha-trypsin inhibitor heavy chain H2) and C5 (complement C5).

Diabetic retinopathy can be classified into early stage, non-proliferative diabetic retinopathy (NPDR) and late-stage, proliferative diabetic retinopathy (PDR). The mechanisms of non-proliferative diabetic retinopathy and proliferative diabetic retinopathy differ from each other in that blood vessels do not develop in non-proliferative diabetic retinopathy, but develop in proliferative diabetic retinopathy. Because non-proliferative diabetic retinopathy must progress to proliferative diabetic retinopathy, a marker known as a diagnostic marker for proliferative diabetic retinopathy must be able to be used as a diagnostic marker for non-proliferative diabetic retinopathy. A diagnostic marker for non-proliferative diabetic retinopathy, which is capable of diagnosing diabetic retinopathy in an early stage, can specifically diagnose both non-proliferative diabetic retinopathy and proliferative diabetic retinopathy.

The present inventors have found that C7, ITIH2 and C5 can be used as diagnostic markers for diabetic retinopathy, as described below.

Specifically, as described in an example of the present invention, biomarker candidates were screened by data mining, and biomarkers were selected from the screened biomarker candidates by a validation stage. From the selected biomarkers, three markers (C7, ITIH2 and C5) specific to NPDR were finally selected.

In another example of the present invention, using plasma samples obtained from a normal control group (subject having no diabetic retinopathy) and a subject having NPDR, the effectiveness of the three selected markers specific to NPDR was verified.

In another aspect, the present invention provides a composition for diagnosing diabetic retinopathy, which comprises an agent for measuring the mRNA or protein level of at least one gene selected from among C7, ITIH2 and C5.

C7 (complement component C7) functions to control an antigen-antibody immune reaction in the human body and forms a membrane attack complex (MAC) to lyse pathogens. According to gene ontology classification, it is a protein that involved in immune reactions and lysis, and the genetic information thereof can be found in GeneBank, Uniprot, etc. However, the direct relationship of C7 with diabetic retinopathy has not yet been known.

According to gene ontology classification, ITIH2 (inter-alpha-trypsin inhibitor heavy chain H2) is a protein that is involved in hyaluronan metabolism and functions to carry hyaluronan in blood, and the genetic information thereof can be found in GeneBank, Uniprot, etc. However, the direct relationship of ITIH2 with diabetic retinopathy has not yet been known.

C5 (complement C5) functions to control an antigen-antibody immune reaction in the human body and forms a membrane attack complex (MAC) to lyse pathogens. According to gene ontology classification, it is a protein that involved in immune reactions and lysis, and the genetic information thereof can be found in GeneBank, Uniprot, etc. However, the direct relationship of C5 with diabetic retinopathy has not yet been known.

C7 (complement component C7), ITIH2 (inter-alpha-trypsin inhibitor heavy chain H2) and C5 (complement C5) all have a characteristic in that the expression levels thereof in a subject having diabetic retinopathy decrease compared to those in a normal control group (subject having no diabetic retinopathy) or a subject having diabetic retinopathy.

The composition of the present invention may be a composition for diagnosing diabetic retinopathy, which comprises an agent for measuring the mRNA or protein level of at least one gene selected from among C7 (complement component C7), ITIH2 (inter-alpha-trypsin inhibitor heavy chain H2) and C5 (complement C5).

As used herein, the expression "measuring the mRNA expression level" means measuring the level of mRNA by determining the presence and expression level of mRNA of the diabetic retinopathy diagnostic genes in a biological sample isolated from a subject suspected of having diabetic retinopathy in order to diagnose diabetic retinopathy. Analysis methods for measuring the level of mRNA include, but are not limited to, reverse transcription-polymerase chain reaction (RT-PCR), competitive RT-PCR, real-time RT-PCR, RNase protection assay (RPA), Northern blotting, DNA chip-based assays, etc.

The agent for measuring the mRNA level of the genes is preferably a primer pair or a probe. Because the nucleotide sequences of the genes are known in GeneBank and the like, a person skilled in the art can design a probe or a primer pair for amplifying a specific region of each of the genes based on the sequences of the genes.

Preferably, the agent for measuring the mRNA level of the genes may include a primer pair, a probe or an antisense nucleotide, which binds specifically to at least one gene selected from among C7, ITIH2 and C5.

As used herein, the term "primer pair" refers to a primer pair consisting of forward and reverse primers that recognize the sequence of a target gene. Preferably, it is a primer pair that gives analysis results with specificity and sensitivity. Because the nucleotide sequence of a primer does not match a non-targeted sequence in a sample, the primer can show high specificity when it amplifies only a target gene sequence containing a complementary primer binding site without causing non-specific amplification.

As used herein, the term "probe" refers to a substance capable of binding specifically to the target substance to be detected in a sample in order to specifically identify the presence of the target substance in the sample. The probe molecule that is used in the present invention is not specifically limited, as long as it is a substance that is generally used in the art. Preferably, it may be PNA (peptide nucleic acid), LNA (locked nucleic acid), a peptide, a polypeptide, a protein, RNA or DNA. More preferably, it is PNA. More specifically, the probe may be a biomaterial derived from an organism, an analogue thereof, or a material prepared ex vivo, and examples thereof include enzymes, proteins, antibodies, microorganisms, animal/plant cells and organs, neural cells, DNA, and RNA. Examples of DNA include cDNA, genomic DNA, and oligonucleotides, examples of RNA include genomic RNA, mRNA, and oligonucleotides, and examples of proteins include antibodies, antigens, enzymes, peptides and the like.

As used herein, the term "antisense" refers to an oligomer having a sequence of nucleotide bases and a subunit-to-subunit backbone that allows the antisense oligomer to hybridize to a target sequence in an RNA by Watson-Crick base pairing, to form an RNA/oligomer heteroduplex within the target sequence, typically with an mRNA. The oligomer may have exact sequence complementarity to the target sequence or near complementarity.

As used herein, the expression "measuring the protein expression level" refers to a process of determining the presence and expression level of the protein of the diabetic retinopathy diagnostic gene in a biological sample in order to diagnose diabetic retinopathy. The expression level of the protein can be measured using an antibody, an interacting protein, a ligand, nanoparticles or an aptamer, which binds specifically to the protein or peptide fragment of the gene. In addition, all detection means having a specific affinity for the protein or peptide fragment of the gene may be used to measure the protein expression level. Preferably, the protein expression level is measured without using an antibody, an interacting protein, a ligand, nanoparticles or an aptamer.

Methods for measuring and comparatively analyzing the protein expression level include, but are not limited to, protein chip-based analysis, immunoassay, ligand binding assay, MALDI-TOF (matrix desorption/ionization time of flight mass spectrometry) analysis, SELDI-TOF (surface enhanced laser desorption/ionization time of flight mass spectrometry) analysis, radioactive immunoassay, radioimmunodiffusion, ouchterlony immunodiffusion, rocket immunoelectrophoresis, immunohistostaining, complement fixation assay, two-dimensional electrophoresis, liquid chromatography-mass spectrometry (LC-MS), LC-MS/MS (liquid chromatography-mass spectrometry/mass spectrometry), Western blotting, and ELISA (enzyme linked immunosorbentassay).

Preferably, the agent for measuring the protein level may include an antibody, an interacting protein, a ligand, nanoparticles or an aptamer, which binds specifically to at least one gene selected from among C7, ITIH2 and C5.

As used herein, the term "antibody" refers to a specific protein molecule that is directed to an antigenic site. In view of the purpose of the present invention, the term "antibody" refers to an antibody that binds specifically to at least one protein selected from among C7, ITIH12 and C5. Examples of the antibody include polyclonal antibodies, monoclonal antibodies and recombinant antibodies. Antibodies can easily be produced using technology widely known in the art. In addition, antibodies useful in the present invention include functional fragments of antibody molecules as well as complete forms having two full-length light chains and two full-length heavy chains. The expression "functional fragments of antibody molecules" refers to fragments retaining at least an antigen-binding function, and examples of the functional fragments of antibody molecules include Fab, F(ab'), F(ab')2, Fv and the like.

As used herein, the term "aptamer" refers to a biopolymer material that three-dimensionally binds to a specific target protein in the form of single-stranded or double-stranded DNA or RNA to inhibit protein-protein interaction and binds to various target molecules. Typically, aptamers are small nucleic acids ranging from 15-50 bases in length that fold into defined secondary and tertiary structures, such as stem-loops. It is preferred that the aptamers bind the target high-expression or low-expression protein with a $k_d$ less than $10^{-6}$, $10^{-8}$, $10^{-10}$, or $10^{-12}$ M. Aptamers can bind the target high-expression or low-expression protein with a very high degree of specificity. Aptamers may be comprised of multiple ribonucleotide units, deoxyribonucleotide units, or a mixture of both types of nucleotide residues. In addition, aptamers may further comprise one or more modified bases, sugars or phosphate backbone units.

In another aspect, the present invention provides a kit for diagnosing diabetic retinopathy, which comprises the above-described marker or composition for diagnosing diabetic retinopathy. Preferably, the kit may be a RT-PCR kit, a DNA chip kit, an ELISA kit, a protein chip kit, a rapid kit or a MRM (multiple reaction monitoring) kit.

Preferably, the kit for diagnosing diabetic retinopathy may further comprise a composition, a solution or a device, which contains one or more different components suitable for analysis.

Preferably, the diagnostic kit may be a diagnostic kit comprising essential elements required for performing RT-PCR. The RT-PCR kit comprises a primer pair specific to each of the marker genes. The primer is a nucleotide having a sequence specific to the nucleotide sequence of each of the genes and is about 7-50 bp in length, and preferably about 10-30 bp in length. In addition, the kit may include a primer specific to the nucleotide sequence of a control gene. In addition, the RT-PCR kit may include a test tube or other appropriate container, a reaction buffer (various pHs and magnesium concentrations), deoxynucleotides (dNTPs), enzymes such as Taq-polymerase and reverse transcriptase, DNAse, a RNAse inhibitor, DEPC-water, sterilized water, etc.

Preferably, the kit may be a diagnostic kit comprising essential elements required for performing DNA chip assay. The DNA chip kit may include a substrate having immobilized thereon a cDNA or oligonucleotide corresponding to the gene or its fragment, a reagent for constructing a fluorescence-labeled probe, an agent, an enzyme and the like. In addition, the substrate may comprise a cDNA or oligonucleotide corresponding to a control gene or its fragment.

Preferably, the kit may be a diagnostic kit comprising essential elements required for performing ELISA. The ELISA kit includes an antibody, an interacting protein, a ligand, nanoparticles or an aptamer, which binds specifically to the protein or its peptide fragment. The antibody has a high specificity and affinity for each of the marker proteins and shows little or no cross-reactivity with other proteins. It is a monoclonal antibody, a polyclonal antibody or a recombinant antibody. Also, the ELISA kit may include an interacting protein, a ligand, nanoparticles or an aptamer, which binds specifically to the protein or its peptide fragment, as well as an antibody specific to a control protein. In addition, the ELISA kit may include reagents which may detect bound antibodies, such as for example labelled secondary antibodies, chromophores, enzymes (e.g., conjugated with antibodies) and the substrates thereof or other substances which are capable of binding antibodies.

In still another aspect, the present invention provides a method for providing information for diagnosis of diabetic retinopathy using the above-described diagnostic marker, composition or kit.

Preferably, the method for providing information may be a method comprising the steps of: measuring the expression level of at least one gene or its protein, selected from among C7 (complement component C7), ITIH2 (inter-alpha-trypsin inhibitor heavy chain H2) and C5 (complement C5), in a biological sample isolated from a subject suspected of having diabetic retinopathy; and comparing the expression level of the gene or its protein with that in a normal control sample. The expression level in the normal control sample may be the expression level of the gene or its protein in a sample isolated from a subject having non-proliferative diabetic retinopathy.

Examples of the biological sample that is used in the present invention include, but are not limited to, tissue, cells, whole blood, serum, plasma, saliva, cerebrospinal fluid, and urine, in which the expression level of the gene or its protein is changed by the onset of diabetic retinopathy.

In addition, the method may further include a step of diagnosing the biological sample as diabetic retinopathy when the expression level of the C7, ITIH2 or C5 gene or its protein in the biological sample decreases compared to that in the sample isolated from the subject having non-proliferative diabetic retinopathy.

Preferably, the expression level of the gene can be determined by measuring and comparing of the expression level of mRNA.

The measurement or comparison of the mRNA expression level may be performed using reverse transcription-polymerase chain reaction (RT-PCR), competitive RT-PCR, real-time RT-PCR, RNase protection assay (RPA), Northern blotting, DNA chip-based assays, etc., but is not limited thereto. According to the above assay methods, the expression level of mRNA in the normal control sample and the expression level of mRNA in a diabetic retinopathy patient can be determined, and the onset of diabetic retinopathy can be diagnosed or predicted by comparing the expression levels of mRNA.

Preferably, the expression levels of the protein can be measured and compared using an interacting protein, a ligand, nanoparticles or an aptamer, which binds specifically to the protein or its peptide fragment. Specifically, the antibody and the protein in the biological sample are allowed to form an antigen-antibody complex which is to be detected.

As used herein, the term "antigen-antibody complex" means a combination of a protein antigen for determining the presence or absence of the protein of interest in a sample and an antibody recognizing the protein antigen. The detection of the antigen-antibody complex may be performed by any known methods, such as spectrophotometric, photochemical, biochemical, immunochemical, electrical, light-absorbing, chemical, or other methods.

Preferably, the measurement and comparison of the protein expression levels can be performed by measuring and comparing the protein expression levels without using an antibody.

For the purpose of the present invention, methods for measuring and comparatively analyzing the protein expression level include, but are not limited to, protein chip-based analysis, immunoassay, ligand binding assay, MALDI-TOF (matrix desorption/ionization time of flight mass spectrometry) analysis, SELDI-TOF (surface enhanced laser desorption/ionization time of flight mass spectrometry) analysis, radioactive immunoassay, radioimmunodiffusion, ouchterlony immunodiffusion, rocket immunoelectrophoresis, immunohistostaining, complement fixation assay, two-dimensional electrophoresis, liquid chromatography-mass spectrometry (LC-MS), LC-MS/MS (liquid chromatography-mass spectrometry/mass spectrometry), Western blotting, and ELISA (enzyme linked immunosorbentassay).

In a specific embodiment of the present invention, the LC-MRM method may be used to measure and compare the expression levels of the C7, ITIH2 and C5 proteins.

Specifically, the protein in a biological sample isolated from a subject suspected of having diabetic retinopathy is passed through an LC analysis column with a solution of 5 vol % distilled water, 95 vol % acetonitrile and 0.1 vol % formic acid along a concentration gradient from 5% to 85% for 30 minutes. Because the ability to decompose a specific material can vary depending on the mixing ratio of the components in the solution, the a concentration gradient is performed, and thus the above range is the optimum range selected in order to separate various proteins at the same time.

In mass spectrometry, quantitative analysis is performed by MRM (multiple reaction monitoring) in the MS/MS mode. SIM (selected ion monitoring) is a method that uses ions produced by bombardment on the source region of a mass spectrometer, whereas MRM is a method that uses ions obtained by selecting specific ions from broken ions and bombarding the selected ions through the source of another connected MS. More specifically, SIM has a problem in that the selected ions can interfere with quantification when these ions are also detected in plasma. However, in MRM, when ions are broken once more, they show a differential tendency while the molecular structure thereof changes, even though these ions have the same mass. Thus, when these broken ions are used as ions for quantification, interfering peaks can be removed from the background, and thus a clearer base line can be obtained. Thus, when the MRM mode is used in mass spectrometry, substances of interest can be simultaneously analyzed with high sensitivity.

Using the above analysis methods, the expression level of the protein of interest in a subject having diabetic retinopathy can be compared with the expression level of the protein in a normal control, and the onset of diabetic retinopathy can be diagnosed by determining a significant increase or decrease in the expression level of the diabetic retinopathy marker gene. In addition, a biological sample can be diagnosed as non-proliferative diabetic retinopathy when the expression level of the inventive marker gene or its protein in the biological sample decreases compared to the expression level of the marker gene or its protein in a sample isolated from a proliferative diabetic retinopathy patient.

Hereinafter, the present invention will be described in further detail with reference to examples. It is to be understood, however, that these examples are for illustrative purposes only and are not intended to limit the scope of the present invention.

Example 1: Selection of Proteins Whose Expression Increases or Decreases in Diabetic Retinopathy Biomarker candidates were screened by data mining, and a validation stage was performed for the screened biomarker candidates. In the data mining, a total of 1,010 protein data (identification and quantitation information) related to diabetic retinopathy (DR) were collected. Based on the frequency of the collected data, candidate proteins for MRM validation were screened.

In this Example, proteins observed at a frequency of 7 or more were selected, and a total of 128 proteins were primarily selected. From the 128 selected proteins, a total of 28 proteins were selected using a pooling sample according to actual detection transition, and the transition of each of the proteins was selected. Then, using a total of 60 individual samples (NoDR: 20, MI NPDR: 20, and MO NPDR: 20), whether the 28 selected proteins were specifically expressed was analyzed by MRM. In this Example, analysis was performed using each of a control sample (sample isolated from a diabetic patient having no diabetic retinopathy), mild NPDR (MI NPDR) and moderate NPDR (MO NPDR), and as a result, three proteins whose expression specifically decreased in moderate NPDR were selected from among the 28 proteins (Table 1).

TABLE 1

| SEQ ID NO. | Protein name | Expression pattern | UniProt | Gene Accession |
|---|---|---|---|---|
| 1 | C7 (complement component C7) | Expression decreased | P10643 | NM_000587 |
| 2 | ITIH2 (inter-alpha-trypsin inhibitor heavy chain H2) | Expression decreased | P19823 | NM_002216 |
| 3 | C5 (complement C5) | Expression decreased | P01031 | NM_001735 |

Example 2: Section of Patients and Collection of Plasma

LC-MS/MS test samples were obtained from the plasma samples of 40 non-proliferative diabetic retinopathy patients and the plasma samples of control patients (diabetic patients having no diabetic retinopathy; NoDR). The clinical characteristics of the 40 non-proliferative diabetic retinopathy patients and the control patients are shown in Table 2 below.

TABLE 2

| Groups | Sex (female/male) | Age | Years after diagnosis of DM | Hypertension (Hyper./total) | Plasma concentration (µg/µl) | CV (%) of plasma concentration |
|---|---|---|---|---|---|---|
| NoDR | 10/10 | 63.8 ± 9.5 | 12.3 ± 5.94 | 8/20 | 79.26 | 9.2 |
| MI NPDR | 10/10 | 61.4 ± 6.7 | 16.9 ± 6.0 | 9/20 | 68.04 | 9.3 |
| MO NPDR | 10/10 | 60.6 ± 9.9 | 15.9 ± 5.91 | 15/20 | 74.13 | 8.3 |

Example 3: Pretreatment of Plasma Samples

The plasma samples were quantified by the Bradford method, and 200 µg of each of the plasma samples was denatured with urea. The denatured samples were reduced and alkylated using DTT and iodoacetic acid. Then, each of the samples was treated with trypsin at a ratio of 50:1 (protein: trypsin, w/w) to convert the proteins into peptides. The peptides were desalted using C18 ZipTip and freeze-dried. Each of the proteins was dissolved in solution A (95% distilled water, 5% acetonitrile and 0.1% formic acid), and the solution was spiked with 50 fmol of beta-galactosidase peptide as an internal standard, and then analyzed by MRM.

Example 4: Selection of Transition

In order to select the transition of the proteins, each of the proteins selected in Example 1 was analyzed by MS/MS. Based on the results of the analysis, a representative peptide for each of the proteins was selected (Q1 transition), and from fragmentation ions generated by electrically breaking the peptide, an ion having the highest intensity (Q3) was selected. Then, at least two peptides were selected for each of the proteins, and at least two fragmentation ions were selected for each of the peptides to determine the Q1/Q3 value. In the present invention, transitions were selected using the Skyline (version 1.1.0.2905) program, and some transitions which were difficult to experimentally select, due to low peak intensity, were selected using the MIDAS (MRM-initiated detection and sequencing) workflow program (MRMPliot, version 2.0, Appliedbiosystems, USA). In addition, transitions which were not detected even by the MIDAS workflow program were selected by selecting peptides, observed at a high frequency, using the peptide Atlas database.

Example 5: LC and MRM

LC was performed using MDLC nanoflow TempoLC (MDS Corp.). For the separation of peptides, C18 resin having a diameter of 3 µm and a pore size of 200 Å was packed directly into a fused silica capillary column having a length of 15 cm and an inner diameter of 100 µm. 10 µl of the peptide sample was injected directly into an analytical column without passage through a trap column at a flow rate of 400 nl/min. Each of the columns was equilibrated with solution A (95% distilled water, 5% acetonitrile and 0.1% formic acid) for 10 minutes, and then eluted with solution B (5% distilled water, 95% acetonitrile and 0.1% formic acid) along a concentration gradient from 5% to 85% for 30 minutes and at 85% for 5 minutes.

In mass spectrometry, the transitions of the selected proteins were monitored in the MRM mode using the 4000 QTrap system (hybrid triple quadrupole/linear ion trap, Applied Biosystems) at an ion voltage of 2000 Volt, and resolution units at Quadruple 1 (Q1) and Quadruple 3 (Q3) were set. The dwell time for transition was set at 20 milliseconds so that the total cycle time was 2.5 seconds. Nebulizing gas was used at 5 units, and the heater temperature was set at 150° C. during the analysis. To demonstrate variations between batches, 50 fmole of the beta-galactosidase peptide (transition 542.3/636.3) spiked into each of the samples was also monitored. MS was performed in sync with LC for 60 minutes, and MS and LC were driven using Analyst 2.1.2.

Example 6: Data Analysis

For relative quantification, MRM quantification was performed at a total of 8 concentrations (blank, 0.5, 1.0, 5.0, 10.0, 25.0, 50.0 and 100.0 fmol) using beta-palatosidase peptide (transition 542.3/636.3), thereby determining a standard curve. For the result of MRM of each individual, the extract ion chromatography (XIC) of the corresponding MRM transition was produced using MultiQuant (AppliedBiosystems, ver1.0), and the peak area of each transition was calculated and plotted with time. The XIC peak area of each transition was normalized with the XIC peak area of beta-galatosidase peptide (transition 542.3/636.3) as an internal standard, and based on the normalized value, quantitative analysis was performed for each protein. For statistical analysis, an interactive plot and a ROC (receiver operating characteristic) curve were plotted using MedCalc (MedCalc Software, Belgium, version 11.3.3), and ANOVA (analysis of variance) statistical analysis was performed. For the preparation of some plots and t-test analysis, Sigma Plot (Systat Software Inc, USA, version 10.1) was used.

Based on the results of the analysis, three proteins showing a significant difference in the expression level were selected. The interactive plots of the three proteins are shown in FIGS. 3, 5 and 7, and the ROC curves of the three proteins are shown in FIGS. 4, 6 and 8.

Figure 3:
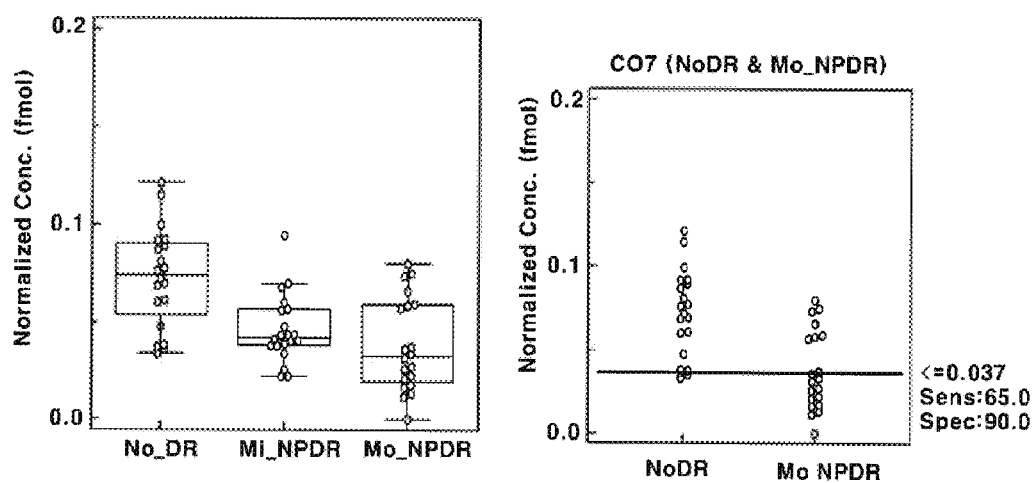
FIG. 3 is a graphic diagram showing the interactive plot of C7 (complement component C7), determined in Example 6 of the present invention.
Figure 4:
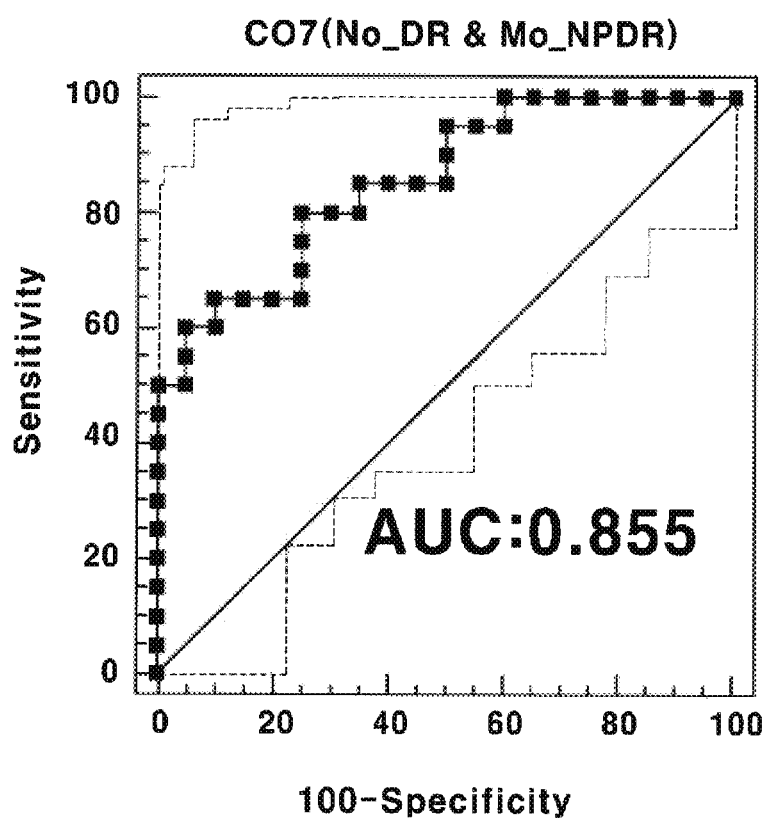
FIG. 4 is a graphic diagram showing the ROC curve of C7, determined in Example 6 of the present invention.

FIG. 3 is a graphic diagram showing the interactive plot of C7 (complement component C7), determined in Example 6 of the present invention, and FIG. 4 is a graphic diagram showing the ROC curve of C7, determined in Example 6 of the present invention. FIG. 5 is a graphic diagram showing the interactive plot of ITIH2 (inter-alpha-trypsin inhibitor heavy chain H2), determined in Example 6 of the present invention, and FIG. 6 is a graphic diagram showing the ROC curve of ITIH2, determined in Example 6 of the present invention. In addition, FIG. 7 is a graphic diagram showing the interactive plot of C5 (complement component C7), determined in Example 6 of the present invention, and FIG. 8 is a graphic diagram showing the ROC curve of C5, determined in Example 6 of the present invention.

Figure 5:
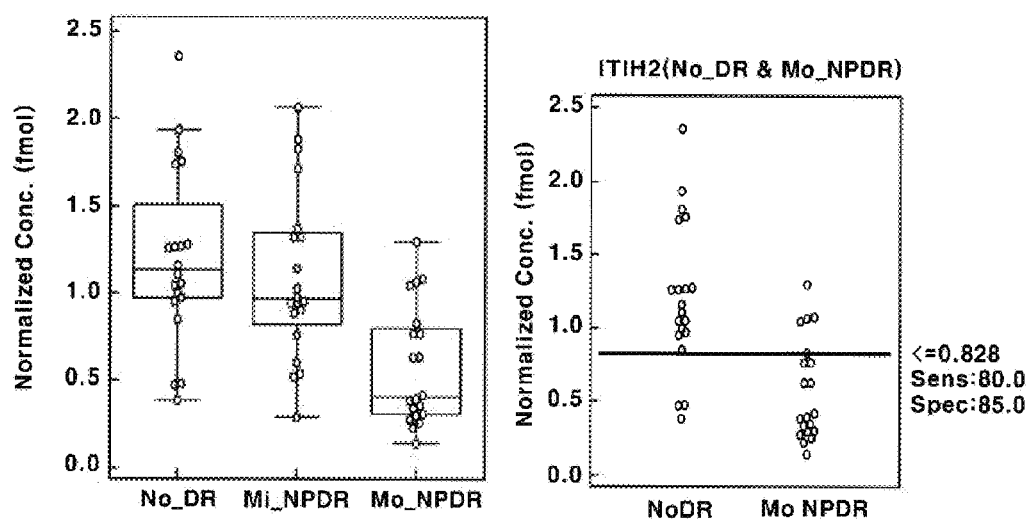
FIG. 5 is a graphic diagram showing the interactive plot of ITIH2 (inter-alpha-trypsin inhibitor heavy chain H2), determined in Example 6 of the present invention.
Figure 7:
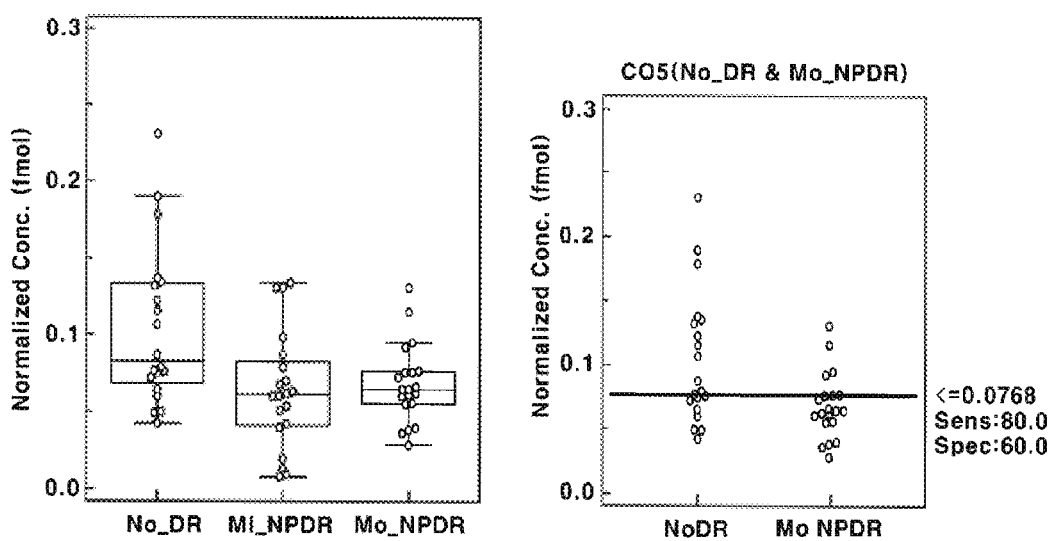
FIG. 7 is a graphic diagram showing the interactive plot of C5 (complement C5), determined in Example 6 of the present invention.

As can be seen in the interactive plots of FIGS. 3, 5 and 7, the result values of quantitative analysis of each of C7, ITIH2 and C5 in the Mi_NPDR and Mo_NPDR samples were generally lower than those in the No_DR sample, suggesting that the expression levels of the proteins in the Mi_NPDR and Mo_NPDR samples decreased compared to those in the No_DR sample. The right graph in each of FIGS. 3, 5 and 7 shows a comparison between the Mo_N-PDR sample and the No_DR sample, and as can be seen therein, the difference in the expression pattern of the proteins between the two samples was more significant. Thus, the expression patterns of C7, ITIH2 and C5 in the Mi_NPDR sample and the Mo_NPDR sample did differ from those in the No_DR sample, suggesting that C7, ITIH12 and C5 can be used as diagnostic markers specific to non-proliferative diabetic retinopathy (including both mild NPDR (MI NPDR) and moderate NPDR (MO NPDR)).

Figure 6:
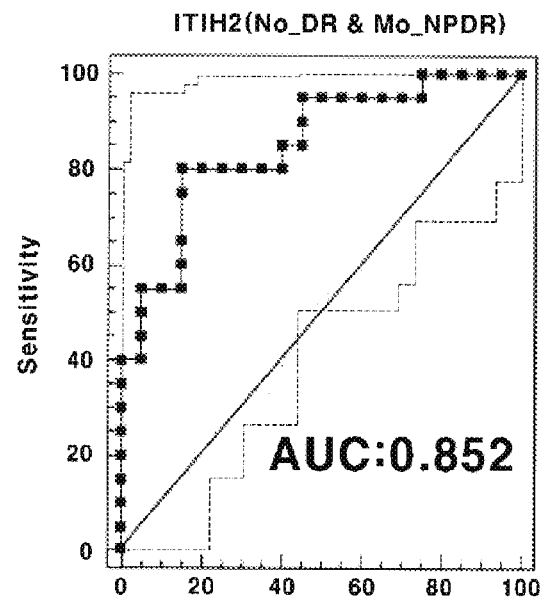
FIG. 6 is a graphic diagram showing the ROC curve of ITIH2, determined in Example 6 of the present invention.
Figure 8:
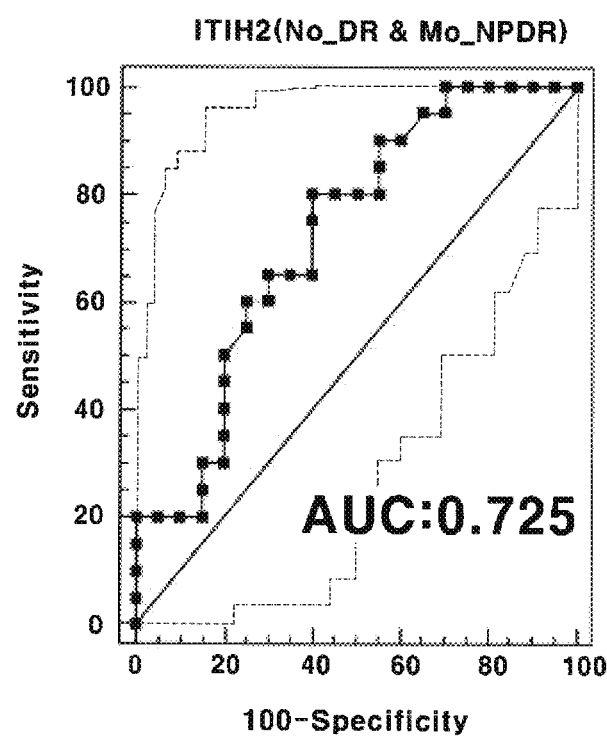
FIG. 8 is a graphic diagram showing the ROC curve of C5, determined in Example 6 of the present invention.

In addition, in the ROC curves of FIGS. 4, 6 and 8, the area defined by the dotted line can be seen as the value of relative quantitative analysis. As can be seen therein, C7, ITIH2 and C5 in the Mo_NPDR sample showed a large area value of about 0.8, suggesting that C7, ITIH2 and C5 have high specificity and sensitivity to the Mo_NPDR sample, and thus can be used as specific markers capable of diagnosing diabetic retinopathy.

As described above, the present invention can provide a marker capable of diagnosing diabetic retinopathy.

According to the present invention, diabetic retinopathy can be early diagnosed and the progression thereof can be effectively predicted or understood by measuring and comparing the expression levels of genes or proteins, the expressions of which increase or decrease in diabetic retinopathy patients.

In addition, when the marker of the present invention is used, diabetic retinopathy can be diagnosed in a non-invasive manner, and thus diabetic retinopathy can be effectively diagnosed in an early stage by a simple method such as a blood or urine test.

Although the preferred embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. A composition for diagnosing diabetic retinopathy, comprising:
   an agent for measuring mRNA or protein level of C7 (complement component C7), wherein the agent for measuring the mRNA or protein level of C7 binds to C7 mRNA or protein expressed in blood; and an agent for measuring mRNA or protein level of ITIH2 (inter-alpha-trypsin inhibitor heavy chain H2), wherein the agent for measuring the mRNA or protein level of ITIH2 binds to ITIH2 mRNA or protein expressed in blood, wherein the agent for measuring mRNA or protein level includes a fluorescence-labeled probe, a fluorescence-labeled antibody, a fluorescence-labeled interacting protein, a fluorescence-labeled ligand, fluorescence-labeled nanoparticles or a fluorescence-labeled aptamer.

2. The composition of claim 1, wherein the diabetic retinopathy is non-proliferative diabetic retinopathy.

3. A kit for diagnosing diabetic retinopathy, which comprises the composition of claim 1.

4. A kit for diagnosing diabetic retinopathy, which comprises the composition of claim 2.

* * * * *